(12) United States Patent
Govari

(10) Patent No.: US 10,506,991 B2
(45) Date of Patent: Dec. 17, 2019

(54) DISPLAYING POSITION AND OPTICAL AXIS OF AN ENDOSCOPE IN AN ANATOMICAL IMAGE

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/693,271

(22) Filed: Aug. 31, 2017

(65) Prior Publication Data
US 2019/0059833 A1 Feb. 28, 2019

(51) Int. Cl.
| | |
|---|---|
| *G06K 9/00* | (2006.01) |
| *A61B 6/12* | (2006.01) |
| *A61B 6/00* | (2006.01) |
| *G06T 7/11* | (2017.01) |
| *G06T 11/20* | (2006.01) |
| *G06T 7/10* | (2017.01) |
| *A61B 6/03* | (2006.01) |

(52) U.S. Cl.
CPC ............... *A61B 6/12* (2013.01); *A61B 6/461* (2013.01); *A61B 6/5211* (2013.01); *G06T 7/10* (2017.01); *G06T 7/11* (2017.01); *G06T 11/20* (2013.01); *A61B 6/032* (2013.01); *G06T 2200/04* (2013.01); *G06T 2207/10068* (2013.01); *G06T 2207/10072* (2013.01); *G06T 2207/10081* (2013.01); *G06T 2207/20021* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 5,391,199 A | 2/1995 | Ben-Haim | |
| 6,016,439 A * | 1/2000 | Acker | A61B 5/06 600/411 |
| 6,239,724 B1 | 5/2001 | Doron et al. | |
| 6,252,599 B1 | 6/2001 | Natsuko et al. | |

(Continued)

FOREIGN PATENT DOCUMENTS

| | | |
|---|---|---|
| WO | WO 96/05768 A1 | 2/1996 |
| WO | WO 2015/149041 A1 | 10/2015 |

OTHER PUBLICATIONS

Rickman et al., "Electromagnetic Navigation-Assisted Bronchoscopy", Operative Techniques in Thoracic and Cardiovascular Surgery, 2014 (Year: 2014).*

(Continued)

*Primary Examiner* — Soo Jin Park
(74) *Attorney, Agent, or Firm* — Frost Brown Todd LLC

(57) ABSTRACT

A method includes, receiving (i) a set of two-dimensional (2D) slices of a segmented three-dimensional (3D) anatomical image of an organ of a patient, and (ii) position signals that are indicative of respective position and orientation of a distal tip of a medical tool in the organ. An optical axis of the medical tool is estimated based on the position signals. A slice that is: (i) oriented at a predefined angle relative to the optical axis, and (ii) includes the position of the distal tip, is selected from among the slices. The selected slice is displayed to a user, together with a marker indicative of the position of the distal tip.

15 Claims, 2 Drawing Sheets

(56) References Cited

U.S. PATENT DOCUMENTS

| | | | |
|---|---|---|---|
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,491,198 B2* | 2/2009 | Kockro | A61B 90/36 606/1 |
| 8,102,416 B2* | 1/2012 | Ito | A61B 34/20 348/65 |
| 9,259,290 B2* | 2/2016 | Jenkins | A61B 34/20 |
| 9,770,216 B2* | 9/2017 | Brown | A61B 6/032 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0159323 A1* | 7/2006 | Sun | A61B 5/0035 382/128 |
| 2008/0091109 A1 | 4/2008 | Abraham | |
| 2009/0012390 A1* | 1/2009 | Pescatore | A61B 6/12 600/425 |
| 2010/0022871 A1 | 1/2010 | De Beni et al. | |
| 2010/0312095 A1* | 12/2010 | Jenkins | A61B 5/415 600/411 |
| 2011/0125006 A1 | 5/2011 | Yamamoto et al. | |
| 2013/0123799 A1 | 5/2013 | Smith et al. | |
| 2014/0051986 A1* | 2/2014 | Zhao | A61B 5/066 600/424 |
| 2014/0187949 A1* | 7/2014 | Zhao | A61B 8/12 600/443 |
| 2014/0344742 A1 | 11/2014 | Wiemker et al. | |
| 2016/0317035 A1* | 11/2016 | Hendriks | A61B 1/2676 |
| 2016/0354057 A1* | 12/2016 | Hansen | A61B 8/0841 |
| 2017/0323473 A1* | 11/2017 | Wright | A61B 34/20 |

OTHER PUBLICATIONS

European Search Report, Extended, and Written Opinion dated Nov. 19, 2018 for Application No. EP 18191681.8, 9 pgs.

Weersink, R.A., "Image Fusion and Visualization," Bioengineering for Surgery: The Critical Engineer Surgeon Interface; Chapter 3, Elsevier, Jan. 1, 2016, pp. 29-58, XP055520638, 30 pgs.

* cited by examiner

DISPLAYING POSITION AND OPTICAL AXIS OF AN ENDOSCOPE IN AN ANATOMICAL IMAGE

FIELD OF THE INVENTION

The present invention relates generally to tracking a medical device in a patient organ, and particularly to methods and systems for navigating an endoscope in the organ without entering restricted sections thereof.

BACKGROUND OF THE INVENTION

Some medical procedures require navigating a medical device between restricted sections of a patient organ.

For example, U.S. Patent Application Publication 2014/0344742 describes system and method that include a processor, and memory coupled to the processor which stores a planning module. A user interface is coupled to the processor and configured to permit a user to select a path through a pathway system. The planning module is configured to upload one or more slices of an image volume corresponding to a user-controlled cursor point guided using the user interface, such that as the path is navigated, the one or more slices are updated in accordance with a depth of the cursor point in the path.

PCT Patent Application Publication WO 2015/149041 describes a system that includes a Q3D endoscope disposed to image a field of view and a processor that produces a Q3D model of a scene and identifies target instruments and structures. The processor is configured to display the scene from a virtual field of view of an instrument, to determine a no fly zone around targets, to determine a predicted path for said instruments or to provide 3D tracking of said instruments.

SUMMARY OF THE INVENTION

An embodiment of the present invention that is described herein provides a method that includes receiving (i) a set of two-dimensional (2D) slices of a segmented three-dimensional (3D) anatomical image of an organ of a patient, and (ii) position signals that are indicative of respective position and orientation of a distal tip of a medical tool in the organ. An optical axis of the medical tool is estimated based on the position signals. A slice that is: (i) oriented at a predefined angle relative to the optical axis, and (ii) includes the position of the distal tip, is selected from among the slices. The selected slice is displayed to a user, together with a marker indicative of the position of the distal tip.

In some embodiments, the predefined angle includes a right angle between the slice and the optical axis. In other embodiments, the method includes identifying one or more selected no-fly zone (NFZ) sections of the organ that are restricted for access of the medical tool, and displaying, in the slice, one or more respective markers indicative of respective sectional views of the one or more selected NFZ sections that fall in the slice. In yet other embodiments, displaying the marker includes providing a warning indication in response to detecting that at least part of the medical tool is within a predefined distance from at least one of the selected NFZ sections.

In an embodiment, the organ includes a nasal sinus, and receiving the set of slices of the segmented anatomical images includes receiving a set of slices of one or more computerized tomography (CT) segmented images of the nasal sinus. In another embodiment, receiving the position signals includes receiving the position signals from a position sensor of a position tracking system, the position sensor is coupled to a distal end of the medical tool.

In some embodiments, the medical tool includes an endoscope. In other embodiments, estimating the optical axis includes estimating, based on a sequence of the position signals, a direction of movement of a distal end of the medical tool.

There is additionally provided, in accordance with an embodiment of the present invention, an apparatus that includes an interface and a processor. The interface is configured to receive (i) a set of two-dimensional (2D) slices of a segmented three-dimensional (3D) anatomical image of an organ of a patient, and (ii) position signals that are indicative of respective position and orientation of a distal tip of a medical tool in the organ. The processor is configured to estimate, based on the position signals, an optical axis of the medical tool, to select, from among the slices, a slice that is: (i) oriented at a predefined angle relative to the optical axis, and (ii) includes the position of the distal tip, and to display the selected slice to a user, together with a marker indicative of the position of the distal tip.

The present invention will be more fully understood from the following detailed description of the embodiments thereof, taken together with the drawings in which:

DETAILED DESCRIPTION OF EMBODIMENTS

Overview

Some medical procedures, such as sinuplasty, may require navigating a medical device, such as an endoscope, in a patient head, without inserting the endoscope to restricted sections of the head, typically for patient safety reasons.

Embodiments of the present invention that are described hereinbelow provide improved methods and systems for navigating an endoscope in the patient head without entering such restricted sections.

In some embodiments, the navigation system receives a set of two-dimensional (2D) slices of a segmented three-dimensional (3D) anatomical image of the patient head, and position signals from a position sensor of a position tracking system. The position signals are indicative of respective position and orientation of a distal tip of the endoscope in the patient head.

In some embodiments, a processor in the navigation system is configured to estimate, based on the position signals, a direction of movement of the distal tip, which typically corresponds to an optical axis of the endoscope. In some embodiments, the processor is further configured to select, from among the 2D slices, a slice that (i) is orthogonal to the optical axis of the endoscope, and (ii) comprises the position of the distal tip.

In some embodiments, the processor is configured to display the selected slice to a user, along with a marker indicative of the position of the distal tip.

During a sinuplasty procedure a physician may select one or more sections in the patient head that are restricted for medical tools. In some embodiments, the processor is configured to store the selected sections in a memory and, when at least one of the restricted sections falls within the displayed slice, to display in the slice markers indicative of the restricted sections. In some embodiments, the processor is further configured to provide a warning indication to the physician, in response to detecting that the distal tip, or any other part of the endoscope, has been moved too close to one or more of the restricted sections, and therefore may cause damage to tissue therein.

The disclosed techniques are particularly important in minimally invasive medical procedures, such as in sinuplasty procedures, carried out in highly branched organs having restricted sections. In such procedures, the disclosed techniques enable accurate navigation to a target location, and increase the patient safety by providing a warning indication that the endoscope may cause damage to tissue in the restricted sections.

System Description

Figure 1:
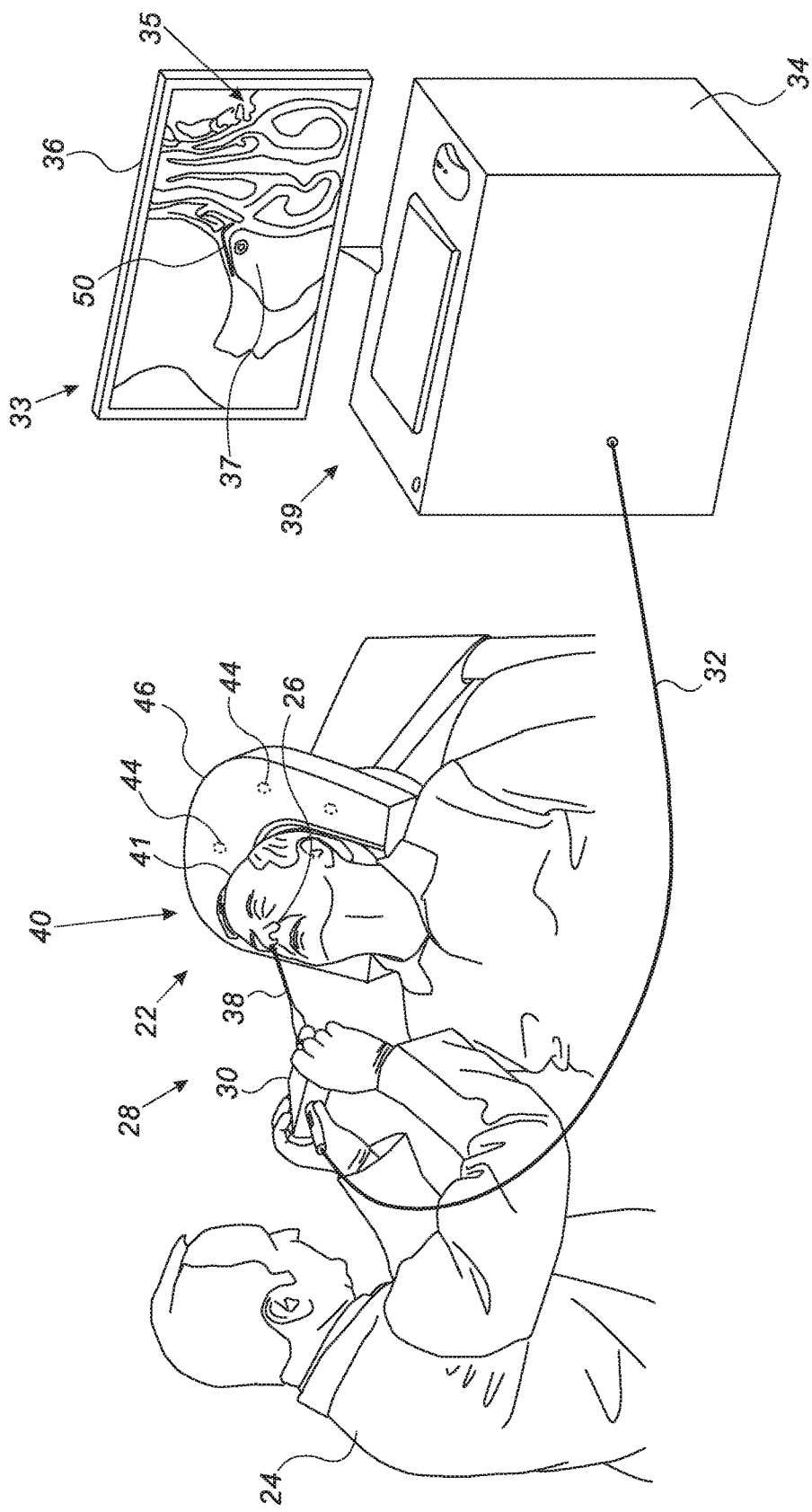
FIG. 1 is a schematic, pictorial illustration of a sinuplasty procedure using a sinuplasty system, in accordance with an embodiment of the present invention.

FIG. 1 is a schematic pictorial illustration of a sinuplasty procedure using a sinuplasty system 20, in accordance with an embodiment of the present invention. In some embodiments, sinuplasty system 20 comprises a medical device, such as an ear-nose-throat (ENT) endoscope 28, which is configured to visualize an ENT section, e.g., a nasal sinus 37, of a patient 22. In the context of the present disclosure and in the claims, the terms "tool" and "device" are used interchangeably and refer to any suitable medical devices used in a respective medical procedure.

In some embodiments, endoscope 28 comprises a distal end 38 having a camera (shown in FIG. 2 below) coupled thereto, which a physician 24 inserts into a nose 26 of patient 22. Endoscope 28 further comprises a handheld apparatus 30, coupled to a proximal end of distal end 38 and configured to assist physician 24 in navigating distal end 38 into sinus 37, so as to acquire images of sinus 37.

In other embodiments, any suitable medical device (not shown), such as a cutter or a suction tool, may be coupled to endoscope 28.

In an embodiment, system 20 further comprises a magnetic position tracking system, which is configured to track the position and orientation of one or more position sensors in the head of patient 22. The magnetic position tracking system comprises magnetic field-generators 44 and a position sensor shown in FIG. 2 below. The position sensor generates position signals in response to the sensed external magnetic fields from the field generators, thereby enabling a processor 34 to map the position and orientation of each sensor as will be described below.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004, 2003/0120150 A1, issued as U.S. Pat. No. 7,729,742 on Jun. 1, 2010 and 2004/0068178 A1, now abandoned, whose disclosures are all incorporated herein by reference.

System 20 further comprises a location pad 40, which comprises field-generators 44 fixed on a frame 46. In the exemplary configuration shown in FIG. 1, pad 40 comprises five field-generators 44 but may comprise any other suitable number of generators 44. Pad 40 further comprises a pillow (not shown) placed under a head 41 of patient 22, such that generators 44 are located at fixed, known positions external to patient 22.

In some embodiments, system 20 comprises a console 33, which comprises a memory (not shown) and a processor 34, typically a general-purpose computer, with suitable front end and interface circuits for receiving signals from endoscope 28 having a magnetic sensor attached thereon (shown in FIG. 2 below), via a cable 32.

In some embodiments, processor 34 is configured to map the position and orientation of the position sensor so as to estimate the position and orientation of a distal tip (shown in FIG. 2 below) of endoscope 28 in the coordinate system of the position tracking system.

In some embodiments, processor 34 is configured to receive one or more anatomical images, such as computerized tomography (CT) images depicting respective segmented two-dimensional (2D) slices of a segmented three-dimensional (3D) anatomical image of a head 41 of a patient 22, obtained using an external CT system (not shown). The term "segmented" refers to displaying various types of tissue identified in each slice by measuring respective attenuation of the tissues in the CT system.

Console 33 further comprises input devices 39 and a user display 36, which is configured to display the data (e.g., images) received from processor 34 or inputs inserted by a user (e.g., physician 24).

In some embodiments, processor 34 is configured to display from among the CT images, one or more selected 2D slices, such as an image 35, on user display 36. In the example of FIG. 1, image 35 is a segmented sectional view of nasal tissue of patient 22, such as sinus 37, which is typically orthogonal to the optical axis of endoscope 28.

In other embodiment, instead of displaying a 2D slice orthogonal to distal tip 60, processor 34 is configured to select, and display on display 36, any 2D slice at any predefined angle relative to the optical axis of endoscope 28. The predefined angle can be constant or may change during the procedure and relative to the organ in question. It will be understood that in practice, the predefined angle may have some variations, for example, due to some latency in processor 34, or due to limited accuracy of the registration between the coordinate systems of the CT system and the position tracking system.

In some embodiments, the segmented CT images are acquired before the sinuplasty procedure, such that physician 24 physician may mark selected sections on one or more of the segmented CT images. For example, the selected sections may be restricted for endoscope 28 or any other medical device.

In an embodiment, processor 34 is further configured to display in image 35, markers indicating the selected sections, e.g., in sinus 37, which are restricted for endoscope 28. In the example of FIG. 1, these restricted sections are referred to and shown as "no-fly zone" (NFZ) 50. The display of the 2D slice and of the markers indicating NFZ 50 are described in detail in FIG. 2 below.

Note that in the context of the present disclosure and in the claims, the terms "restricted" and "NFZ" refer to a section in which the presence of any part of a medical device, such as distal tip 60 of endoscope 28, is not allowed.

Console 33 comprises a driver circuit (not shown), which is configured to drive field-generators 44 with suitable signals so as to generate magnetic fields in a predefined working volume around head 41.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Displaying the Endoscope and No-Fly Zones in a 2D Slice of a CT Image

Figure 2:
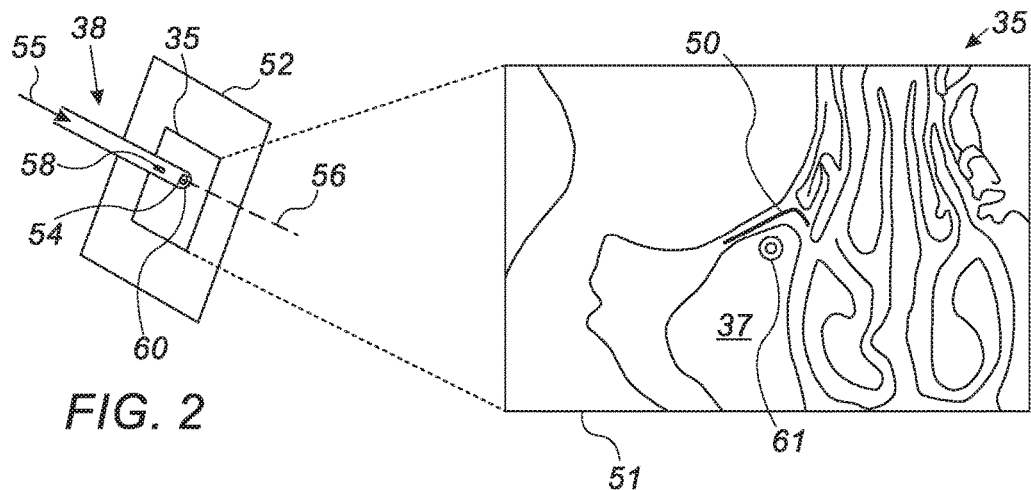
FIG. 2 is a schematic, pictorial illustration of a distal end of an endoscope and an anatomical image, in accordance with an embodiment of the present invention.

FIG. 2 is a schematic, pictorial illustration of distal end 38 of endoscope 28 and image 35, in accordance with an embodiment of the present invention. In some embodiments, a camera 54, which is configured to acquire images of sinus 37 and possibly of other nasal tissue of patient 22, is coupled to a distal tip 60 of endoscope 28.

In some embodiments, a position sensor 54 is coupled to distal end 38 at a predefined location relative to distal tip 60. In some embodiments, position sensor 54 is configured to generate position signals in response to sensing external magnetic fields generated by field generators 44. In an embodiment, processor 34 is configured to register between coordinate systems of the CT system and the position tracking system, so as to map, based on the position signals provided by sensor 54, the position and orientation of distal tip 60 in the coordinate system of the CT system.

In some embodiments, processor 34 is further configured to estimate, based on the position signals, a direction of movement of distal end 38, represented by an arrow 55, which direction typically corresponds to the optical axis of endoscope 28, represented by a dashed line 56.

In some embodiments, processor 34 is configured to select, from among the 2D slices, a slice (e.g., image 35) in a plane 52 that is orthogonal to the optical axis (e.g., dashed line 56), wherein the selected site comprises the position of distal tip 60.

Reference is now made to an inset 51 showing a sectional view on sinus 37 in image 35. In some embodiments, processor 34 is configured to display a marker 61 that indicates the position of distal tip 60 in image 35. In some embodiments, processor 34 is further configured to display marker 61 in the center of image 35, so that physician 24 can see in segmented image 35, tissue located around distal tip 60.

In the description of FIG. 1 above, processor 34 is configured to display any NFZ 50 that falls within image 35 during the movement of distal end 38. In an embodiment, processor 34 is configured to provide a warning indication to physician 24 in response to detecting that distal tip 60, or any other part of endoscope 28, has been moved too close to NFZ 50, and therefor may cause damage to tissue in NFZ 50. In some embodiments, the warning may be presented to physician 24 visually, as shown in image 35 of FIG. 2.

Additionally or alternatively, the warning indication may comprise audio signals or in any other suitable type of alert. In case endoscope 28 is at a sufficient distance from any NFZ, processor 34 is configured to display, on the respective 2D slice, only distal tip 60 and its optical axis, as described above.

Note that during the sinuplasty procedure, physician 24 is typically required to move endoscope 28 within the organ. In order to provide the warning indication, processor 34 is configured, at each location of distal tip 60, to select and display in real-time, a respective 2D slice that is orthogonal to the optical axis of endoscope 28 and that comprises the current location of distal tip 60 and one or more NFZs 50 that fall in the selected 2D slice.

In alternative embodiments, processor 34 is configured to receive images acquired by camera 54 of endoscope 28, and for each such image, to select among the CT images, a 2D slice that best matches the image acquired by camera 54. In these embodiments, the position tracking system (and sensor 58) may be omitted, or alternatively used as control means for verifying the location of the distal tip of endoscope 28. Note that these embodiments require setting specific parameters of camera 54, such as field of view and magnification.

Figure 3:
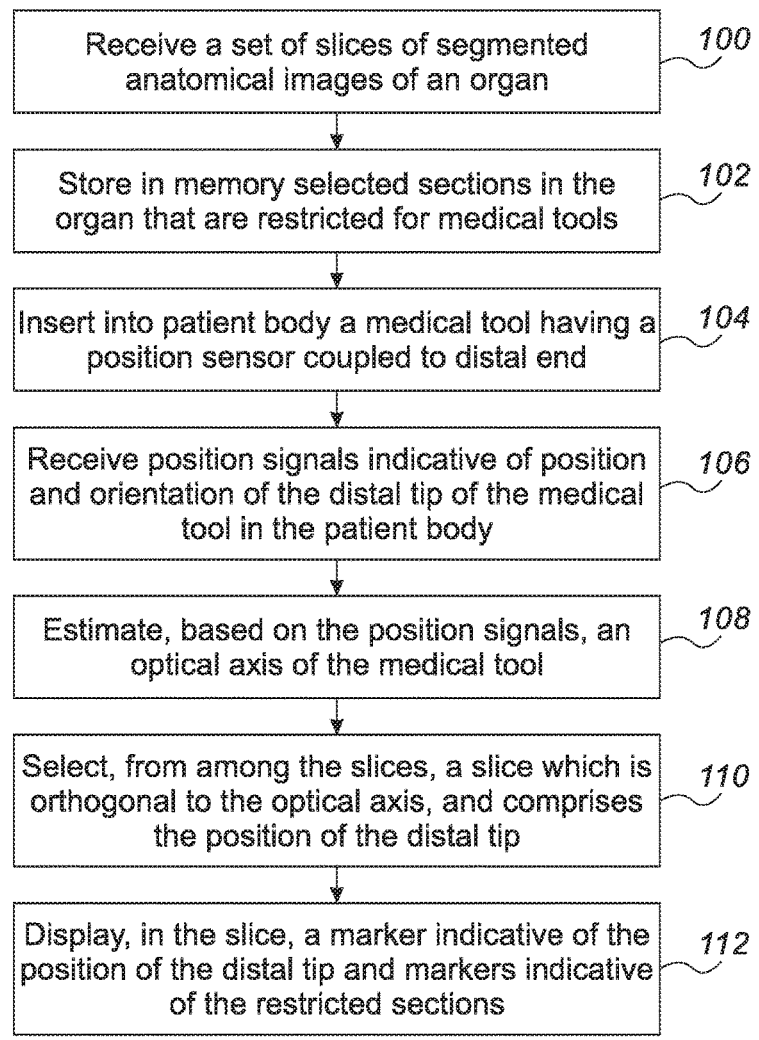
FIG. 3 is a flow chart that schematically illustrates a method for visualizing position and orientation of an endoscope in an anatomical image, in accordance with an embodiment of the present invention.

FIG. 3 is a flow chart that schematically illustrates a method for visualizing position and orientation of distal tip 60 in image 35, in accordance with an embodiment of the present invention. In some embodiments, the method may comprise a preparation procedure carried out before performing the medical (e.g., sinuplasty) procedure, as well as operations carried out during the medical procedure.

The preparation procedure begins with processor 34 receiving from the CT system a set of 2D slices of anatomical images of the nasal tissue of patient 22, at an image acquisition step 100. In some embodiments, the 2D slices are segmented so as to identify various types of tissues in each slice.

At a no-fly zone (NFZ) definition step 102, processor 34 stores in the memory of console 33, sections of NFZs that were predefined by physician 24. Note that NFZ definition step 102 concludes the preparation procedure.

At an endoscope insertion step 106, which is the first step of the medical procedure, physician 24 inserts a medical device into nose 26 of patient 22. In an embodiment, the medical device comprises endoscope 28 and/or any other suitable device configured to carry out a diagnostic and/or treatment procedure in sinus 37 of patient 22. In some embodiments, endoscope 28 comprises position sensor 58 and camera 54 that are coupled to distal end 58 and distal tip 60, respectively.

At a position signals acquisition step 106, processor 34 receives from sensor 58 position signals indicative of the position and orientation of distal tip 60 in sinus 37 of patient 22. In an embodiment, position sensor 58 is coupled to distal end 38 at a predefined offset relative to distal tip 60, in which case processor 34 is configured to estimate, based on the position signals and the predefined offset, the position and orientation of distal tip 60 in sinus 37 or in any other organ of patient 22.

At an optical axis estimation step 108, processor 34 receives a sequence of position signals from sensor 58 corresponding to locations of distal end 38 as physician 24 moves endoscope 28 in head 41 of patient 22. Based on the sequence of the position signals, processor 34 estimates the direction of movement of distal end 38, represented by an arrow 55 in FIG. 2 above, which typically corresponds to the optical axis of endoscope 28.

At a slice selection step 110, processor 34 selects from among the 2D slices, a slice that is orthogonal to the optical axis of endoscope 28 and that comprises the position of distal tip 60, typically at the center of the slice. In some embodiments, processor 34 displays the 2D slice, e.g., as segmented image 35, on display 36.

At a marker display step 112, processor 34 displays in image 35 a marker indicative of the position and optical axis of distal tip 60, such that physician 24 can see a segmented sectional view of distal tip 60 in the organ in question (e.g., sinus 37.)

Although the embodiments described herein mainly address sinuplasty procedures, the methods and systems described herein can also be used in other medical applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   (a) receiving:
      (i) a set of two-dimensional (2D) slices of a segmented three-dimensional (3D) anatomical image of an anatomical structure of a patient, and
      (ii) position signals that are indicative of respective position and orientation of a distal tip of a medical tool in the anatomical structure, wherein the medical tool includes an imaging feature operable to provide a field of view along an optical axis, and wherein the position signals are received while the distal tip is in motion;
   (b) estimating, based on the position signals received while the distal tip is in motion, a direction of movement of the distal tip;
   (c) estimating, based on the estimated direction of movement of the distal tip, the optical axis of the imaging feature of the medical tool;
   (d) selecting, from among the slices, a slice that is:
      (i) oriented at a predefined angle relative to the optical axis, and
      (ii) comprises the position of the distal tip; and
   (e) displaying the selected slice to a user, together with a marker indicative of the position of the distal tip.

2. The method according to claim 1, wherein the predefined angle comprises a right angle between the slice and the optical axis.

3. The method according to claim 1, further comprising identifying one or more selected no-fly zone (NFZ) sections of the anatomical structure that are restricted for access of the medical tool, and, when any of the one or more selected NFZ sections are within a configured distance of the position of the distal tip, displaying, in the slice, one or more respective markers indicative of respective sectional views of the one or more selected NFZ sections that are within the configured distance.

4. The method according to claim 3, wherein displaying the marker comprises providing a warning indication in response to detecting that at least part of the medical tool is within a predefined distance from at least one of the selected NFZ sections.

5. The method according to claim 1, wherein the anatomical structure comprises a nasal sinus, and wherein receiving the set of slices of the segmented anatomical images comprises receiving a set of slices of one or more computerized tomography (CT) segmented images of the nasal sinus.

6. The method according to claim 1, wherein receiving the position signals comprises receiving the position signals from a position sensor of a position tracking system, wherein the position sensor is coupled to a distal end of the medical tool.

7. The method according to claim 1, wherein the medical tool comprises an endoscope.

8. The method according to claim 1, further comprising:
   (a) selecting, from among the slices, a slice that:
      (i) is oriented at the predefined angle relative to the optical axis, and
      (ii) comprises the position of the distal tip at the center of slice;
   (b) displaying the marker indicative of the position of the distal tip at the center of the slice; and
   (c) selecting and displaying a subsequent slice in response to a movement of the distal tip so that the marker indicative of the position of the distal tip is always at the center of a displayed slice.

9. An apparatus, comprising:
   (a) an interface, which is configured to receive:
      (i) a set of two-dimensional (2D) slices of a segmented three-dimensional (3D) anatomical image of an anatomical structure of a patient, and
      (ii) position signals that are indicative of respective position and orientation of a distal tip of a medical tool in the anatomical structure, wherein the medical tool includes an imaging feature operable to provide a field of view along an optical axis; and
   (b) a processor, which is configured to:
      (i) receive position signals while the distal tip is in motion;
      (ii) estimate, based on the position signals, a direction of movement of the distal tip;
      (iii) estimate, based on the estimated direction of movement of the distal tip, the optical axis of the imaging feature of the medical tool;
      (iv) select, from among the slices, a slice that is:
         (A) oriented at a predefined angle relative to the optical axis, and
         (B) comprises the position of the distal tip; and
      (iii) display the selected slice to a user, together with a marker indicative of the position of the distal tip.

10. The apparatus according to claim 9, wherein the predefined angle comprises a right angle between the slice and the optical axis.

11. The apparatus according to claim 9, wherein the processor is configured to identify one or more selected no-fly zone (NFZ) sections of the anatomical structure that are restricted for access of the medical tool, and, when any of the one or more selected NFZ sections are within a configured distance of the position of the distal tip, to display, in the slice, one or more respective markers indicative of respective sectional views of the one or more selected NFZ sections that are within the configured distance.

12. The apparatus according to claim 11, wherein the processor is configured to provide a warning indication in response to detecting that at least part of the medical tool is within a predefined distance from at least one of the selected NFZ sections.

13. The apparatus according to claim 9, wherein the anatomical structure comprises a nasal sinus, and wherein the interface is configured to receive a set of slices of one or more computerized tomography (CT) segmented images of the nasal sinus.

14. The apparatus according to claim 9, wherein the interface is configured to receive the position signals from a position sensor of a position tracking system, wherein the position sensor is coupled to a distal end of the medical tool.

15. The apparatus according to claim 9, wherein the medical tool comprises an endoscope.

* * * * *